United States Patent [19]
Goe et al.

[11] Patent Number: 5,221,747
[45] Date of Patent: Jun. 22, 1993

[54] IMPROVED PROCESS AND CATALYST FOR THE PREPARATION OF 2,2' BIPYRIDYLS

[75] Inventors: Gerald R. Goe, Greenwood; Charles K. McGill, Indianapolis; Angela R. Sherman, Lebanon, all of Ind.

[73] Assignee: Reilly Industries, Inc., Indianapolis, Ind.

[21] Appl. No.: 896,740

[22] Filed: Jun. 9, 1992

Related U.S. Application Data

[63] Continuation of Ser. No. 554,804, Jul. 18, 1990, abandoned, which is a continuation-in-part of Ser. No. 299,789, Jan. 19, 1989, Pat. No. 4,966,972.

[51] Int. Cl.$^5$ ............................................. C07D 401/04
[52] U.S. Cl. ..................................... 546/260; 546/257
[58] Field of Search ......................... 546/255, 257, 260

[56] References Cited

U.S. PATENT DOCUMENTS

| | | | |
|---|---|---|---|
| 2,526,718 | 10/1950 | Wheeler | 546/255 |
| 3,053,846 | 9/1962 | Varcoe | 546/255 |
| 3,152,137 | 10/1964 | Lang et al. | 546/255 |
| 3,560,404 | 2/1971 | Jung | 546/255 |
| 3,697,534 | 10/1972 | Waddan et al. | 546/255 |
| 3,822,279 | 7/1974 | Joy et al. | 546/255 |

FOREIGN PATENT DOCUMENTS

| | | | |
|---|---|---|---|
| 899015 | 6/1962 | United Kingdom | 546/255 |
| 948956 | 9/1962 | United Kingdom | 546/255 |
| 1014076 | 6/1963 | United Kingdom | 546/255 |
| 1009895 | 11/1965 | United Kingdom | 546/255 |
| 1060661 | 3/1967 | United Kingdom | 546/255 |
| 1202711 | 1/1968 | United Kingdom | 546/255 |
| 1377213 | 12/1974 | United Kingdom | 546/255 |

OTHER PUBLICATIONS

G. M. Badger & W. H. F. Sasse, Adv. Heterocyclic Chem. 2, 179 (1963).
W. H. F. Sasse, Org. Syn. Coll., 5, p. 102 (1973).
R. Habermehl, Chem. Eng. Progress, Feb. 1988, pp. 16–19.
A. Agoos, Chemical Week, Dec. 10, 1986, pp. 44–47.
J. P. Wibaut & H. D. Tjeenk Willink, "A Method of Synthesis of 2,2'-Dipyridyl by Catalytic Dehydrogenation of Pyridine Under Pressure," Recueil des Travaux Chimiques des Pays-Bas, vol. 50, 1931, pp. 287–290.
Chem. Abstr. vol. 78, 111132z (1973).

*Primary Examiner*—David B. Springer
*Attorney, Agent, or Firm*—Woodard, Emhardt, Naughton, Moriarty & McNett

[57] ABSTRACT

Processes for the preparation of 2,2'-bipyridyls by reacting a pyridine base in the presence of a nickel catalyst which comprises a significant amount of elemental nickel bound on a suitable support. In one embodiment the coupling reaction takes place in several reactor designs at a temperature of about 200°–240° C. and a pressure sufficient to maintain at least some of the base in a liquid state during the reaction. In other preferred embodiments, processes for preparing 2,2'-bipyridyls are conducted at a temperature between about 175°–240° C. These latter processes require that the nickel have a high specific Ni surface area.

25 Claims, 2 Drawing Sheets

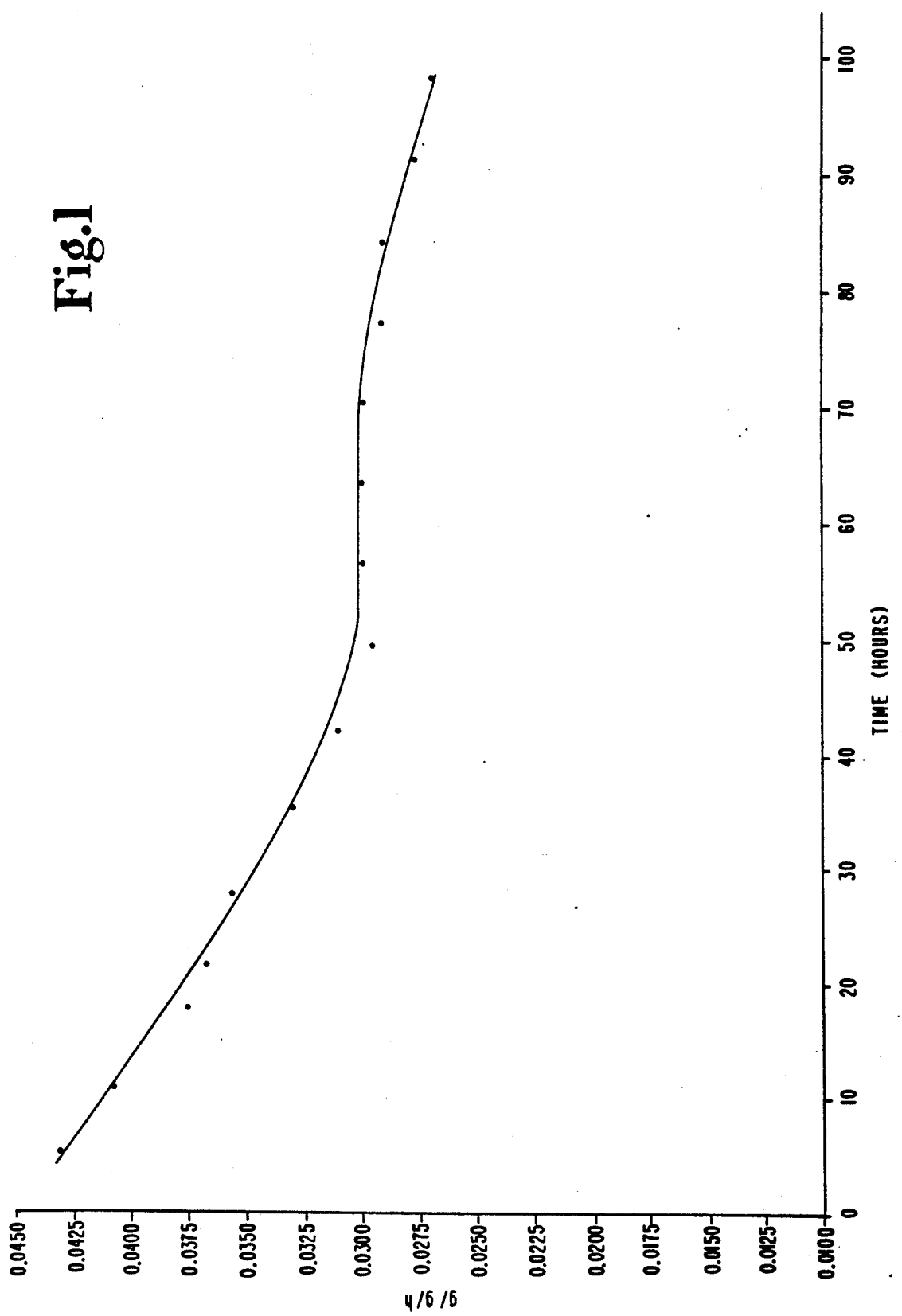

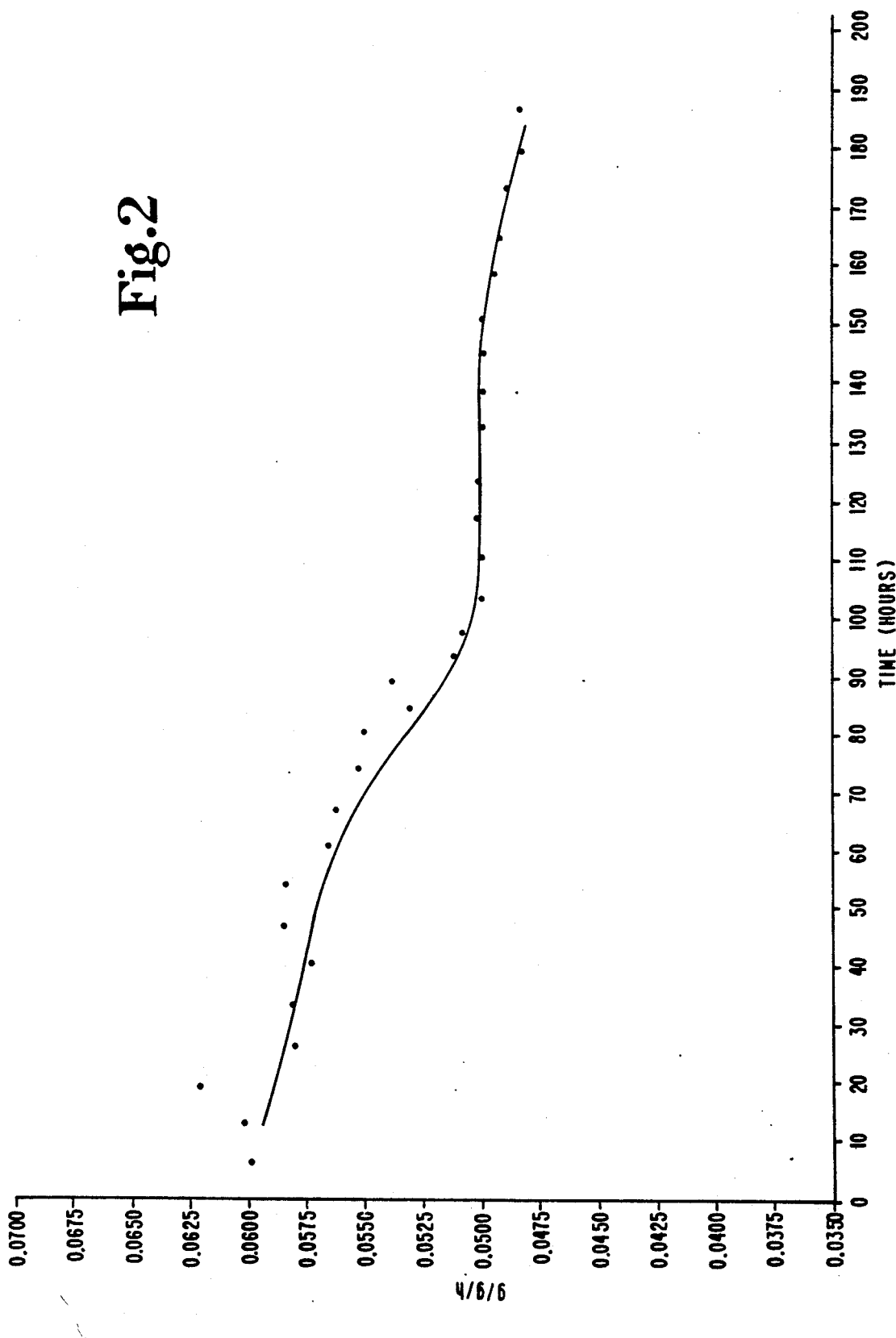

IMPROVED PROCESS AND CATALYST FOR THE PREPARATION OF 2,2' BIPYRIDYLS

This application is a continuation of application Ser. No. 07/554,804, filed Jul. 18, 1990, now abandoned which is a continuation-in-part of U.S. patent application Ser. No. 299,789, filed January 19, 1989, now U.S. Pat. No. 4,966,972.

BACKGROUND OF THE INVENTION

The present invention relates generally to 2,2'-bipyridyl compounds, and more particularly to improved processes for the preparation of 2,2'-bipyridyls which are characterized by the novel use of supported elemental nickel catalysts and methods for reactivating and for extending the useful life of the same.

2,2'-Bipyridyl compounds are among the most useful of pyridine derivatives. They have demonstrated significant economic and technological importance as chelating agents and paint additives and in improved coating compositions. See G. M. Badger & W. H. F. Sasse, Adv. Heterocyclic Chem. 2, 179 (1963) and U.S. Pat. No. 2,526,718 to G. K. Wheeler. They are also widely used to form bridged quaternary salts, commonly known as Diquats which have important herbicidal properties. See L. A. Summers, "The Bipyridinium Herbicides," Academic Press (1980).

Although other routes to 2,2'-bipyridyls have been reported, one of the more advantageous syntheses has been the action of a Raney nickel metal catalyst on pyridine at elevated temperatures. The importance of this catalyst for other reactions harkens back to the early work of Dr. Murray Raney, who originally described the formation and use of a skeletal nickel prepared by treating a nickel aluminum alloy ("Raney alloy") with a caustic material such as sodium hydroxide to leach out the aluminum metal. The resulting skeletal nickel structure has a high surface area compared to other nickel forms, and has been the catalyst of choice for the preparation of 2,2'-bipyridyls from pyridine bases. A primary focus in this area has in turn been to characterize the most preferred ratio of nickel to aluminum in the Raney alloy used and to develop devices and techniques to optimize the conditions and use of the Raney nickel catalyst once made. See, e.g., U.S. Pat. No. 3,822,279 to Joy et al.; Chem. Abstr. vol. 78, 111132z (1973); U.S. Pat. No. 3,053,846 to Varcoe; and Chem. Abstr. Vol. 70, 3770g (1969).

Despite its long-standing predominance, Raney nickel and the processes for its use have also demonstrated significant disadvantages. For example, Raney nickel is a fine powder or a wet sludge which severely complicates its handling and use. Early-on, the 2,2'-bipyridyl reaction was refluxing pyridine on the Raney nickel. It was then discovered that this led to rapid deactivation of the catalyst which has been attributed by some to this prolonged contact with the 2,2'-bipyridyl product itself. See Badger & Sasse, supra p. 199 which reports that "[t]he formation of 2,2'-bipyridine ceases after 50 hours of refluxing." and U.S. Pat. No. 3,053,846 to Varcoe. In later work, alternative reaction schemes and equipment were developed, often focusing on some means whereby pyridine vapors are condensed over and then the resulting hot liquid allowed to stand in contact with the Raney nickel catalyst and slowly filter through the bed in a fashion somewhat similar to a common Soxhlet extractor. This method was thought an improvement because the newly condensing pyridine liquid was intended to displace the previous reaction products in hopes of shortening the period over which the catalyst remains in contact with the 2,2'-bipyridyl formed. Compare, U.S. Pat. No. 3,053,846 which reports a recovery of 0.0231 g of 2,2'-bipyridyl/g Ni/h against W. H. F. Sasse, Org. Syn. Coll., 5, p. 102 (1973) which reports only 0.007 g of 2,2'-bipyridyl produced per g of nickel catalyst per hour. However, while such later processes are feasible, their equipment is often difficult and expensive to build and operate especially when attempting to scale up from the laboratory to the industrial level. Additionally, notwithstanding the many efforts to optimize the use of Raney nickel catalyst, such reactions have demonstrated relatively low rates of conversion to 2,2'-bipyridyls.

In addition to these difficulties, Raney nickel with its skeletal structure is well known to be extremely pyrophoric which presents significant other problems in processing and handling. See R. Habermehl, Chem. Eng. Progress, Feb. 1988, pp. 16-19. Moreover, the caustic substances used to treat Raney alloy in forming the catalyst are commonly aqueous solutions. The Raney nickel is thereby formed as an aqueous paste from which the water must be removed for use in this and many other reactions. This step has proven to be particularly dangerous and expensive, and has been the subject of several patents in the field. For example, the Sasse article in Org. Syn. Coll., 5, reported drying Raney nickel catalyst at 25°-30° C. under partial vacuum (17-20mm) over 4-12 hours while emphasizing caution and noting that when heated under vacuum, Raney nickel catalyst may suddenly give off large quantities of heat and hydrogen resulting in a dangerous explosion. See also, U.S. Pat. No. 3,152,137 to Lang et al. (and corresponding British Patent No. 899,015); and British Patent No. 948,956. The production of Raney alloy itself also involves a costly process requiring extreme conditions, see U.S. Pat. No. 3,822,279 to Joy et al., and disposal of spent Raney nickel catalyst is complicated because it has been identified as a carcinogen. See A. Agoos, Chemical Week, Dec. 10, 1986, pp. 44-47.

Another prevalent problem has been that Raney nickel catalyst tends to suffer a significant loss of activity as the reaction proceeds. Those skilled in this field have yet to discover an effective way to reactivate such a catalyst once it has lost part or all of its activity. One method reported to have some success is to wash the spent Raney nickel with an alcoholic solution of an alkali metal hydroxide such as KOH. See British Patent No. 1,202,711. Still further, although not addressing reactivation, the initial activation of such pyrophoric catalysts was generally discussed in U.S. Pat. No. 3,560,404 to Jung et al. which introduced the catalyst into a non-aqueous organic liquid and in contact with reducing agents such as hydrazine, borohydrides, or hypophosphites until the development of gaseous hydrogen occurred.

The mechanism of this deactivation of Raney nickel through use is not well understood, although as previously discussed some attribute it to prolonged contact of the catalyst with the 2,2'-bipyridyl product. Still other speculation has been that deactivation may be attributed to oxidation of the Raney nickel itself. In any event, deactivation of such catalysts has been a major concern in the field.

Although this background has concentrated thus far on Raney nickel, other types of catalysts have also been reported in the art for the formation of 2,2'-bipyridyls from pyridine bases. Contrary to any perception that oxidation of metal sites deactivates such catalysts, it is interesting to note that British Patent No. 1,377,213 reported the use of various metal oxides including nickel oxide in the formation of 2,2'-bipyridyls. However, the rates of formation for such 2,2'-bipyridyls were low even when the oxides were supported on an inert support and subjected to temperatures and pressures as high as 340° C. and 800 psig. Similarly extreme conditions were used by two researchers who reported obtaining 2,2'-bipyridyl by heating pyridine in the presence of a nickel-alumina catalyst in an autoclave at 320° C. to 325° C. and at pressures of 42 to 44 atmospheres. See J. P. Wibaut and H. D. Tjeenk Willink, "A Method of Synthesis of 2,2'-Dipyridyl by Catalytic Dehydrogenation of Pyridine Under Pressure," Recueil des Travaux Chimiques des Pays-Bas, Vol. 50, 1931, pp. 287-290. Still other reported catalysts include: Ziegler catalysts (U.S. Pat. No. 3,697,534 to Waddan et al.); salts of certain noble metals (British Patent No. 1,014,076 and Badger & Sasse, Adv. Heterocyclic Chem. 2 (1963)); mixtures of nickel and aluminum (Chem. Abstr. Vol. 94, 208723m (1981) and Chem Abstr. Vol. 99, 139784w (1983)); a Grignard reagent (British Patent No. 1,060,661); and certain metal or metal alloy bodies impregnated with an alkaline solution of reducing agent (British Patent No. 1,009,895). All of these have been reported with varying low levels of success.

It is in light of this extensive background that the applicants entered their study in an attempt to discover an improved process and catalyst for the preparation of 2,2'-bipyridyls which are more convenient and effective from all aspects than the prior art Raney nickel and other processes.

SUMMARY OF THE INVENTION

The applicants' invention addresses the various problems of the prior art and provides commercially significant processes and catalysts for the preparation of 2,2'-bipyridyls which avoid the problems inherent with Raney nickel catalysts and at the same time achieve substantial technological and commercial advantages. This is accomplished in one embodiment by reacting a pyridine base in the presence of a nickel catalyst which comprises a significant amount of elemental nickel bound on a suitable high-surface area support. The reaction takes place at a temperature of about 200°-240° C. and at a pressure sufficient to maintain at least some of the base in a liquid state during the reaction.

In various other embodiments, the applicants invention is further characterized by reacting the pyridine base over a supported catalyst in which at least about 30% of the nickel present is in the elemental, nonoxidized state. Temperatures of about 215°-225° C. have been more preferred, with most preferred being about 220° C. from testing thus far Performed. Pressures about equal to or greater than the autogenous pressure of the base at the temperatures of the reaction have also been preferred, depending upon the reactor design being used. Suitable supports have included silica, alumina, kieselguhr, and blends of silica and alumina, with alumina alone being most preferred. Methods for forming the catalysts have included known techniques such as impregnation, precipitation and co-precipitation of a nickel salt on or with the selected support material. Once formed, the supported catalysts have been stable highly porous particles of varying shapes such as pellets, spheres, extrusions and tablets and ranging in size generally from about 1/16-¼ inch in diameter. The catalysts tested have also varied in nickel loading, with most preferred being about 50-60% nickel on alumina as found in catalysts commercially available from the Calsicat Division of Mallinckrodt, Inc. under the series name "Calsicat". Of this nickel present, catalysts with higher amounts exceeding about 75% and approaching about 100% by weight of the nickel in its elemental, activated state have produced the best results.

In other embodiments, the applicants' invention favored two specific routes to preparing 2,2'-bipyridyls in the improved processes outlined above. The first is a liquid phase reaction involving pumping a stream of pyridine base through a standard hot tube reactor. The second is a catalytic distillation-type reaction using a pressure still having a column containing an amount of catalyst and the pyridine base introduced into the column, but with the 2,2'-bipyridyl product taken off the bottom of the still. In each of these reactions, the applicants have also discovered effective methods for extending catalyst life and activity. In the tube reactor, for example, an amount of a methanolic solution of sodium borohydride and ammonium hydroxide was included in the pyridine feed which improved and extended the activity of the supported elemental nickel catalyst A similar improved result was achieved with the catalytic distillation by including an amount of ammonium hydroxide in the pyridine feed and passing gaseous hydrogen up through the catalyst bed in the column.

As an extension of the above work, the applicants' have also discovered that certain types of nickel catalysts can be successfully used to make 2,2'-bipyridyls at temperatures of about 175° up to about 240° C. The catalysts employed in this embodiment comprise a suitable support having bound thereon a significant amount of elemental nickel. Further, the nickel is characterized by having a high specific nickel surface area. In other respects, preferred aspects of this embodiment are similar to those discussed in the embodiments above. The lower temperatures at which effective 2,2'-bipyridyl production can be achieved provide advantages, especially on a commercial scale.

In all cases, the applicants' discoveries avoid many of the mechanical and chemical disadvantages encountered with Raney nickel and other prior art processes by utilizing a catalyst which is more conveniently handled, provides improved rates of 2,2'-bipyridyl formation, and is particularly amenable to extended catalyst life and activity and to scaled-up commercial applications.

Related objects and variations as to the detailed aspects of the invention will become apparent from the following description of the preferred embodiment.

BRIEF DESCRIPTION OF THE DRAWINGS

FIG. 1 is a graphical representation of conversion of pyridine to 2,2'-Bipyridyl (expressed g/g/h) over time in a catalytic distillation where the catalyst was reactivated in situ about midway through the testing, as described in Example 17 below.

FIG. 2 is a graphical representation of conversion of pyridine to 2,2'-bipyridyl (expressed in g/g/h) over time in a catalytic distillation where the pyridine feed was spiked 0.05% by weight with a concentrated ammonium hydroxide solution, and where the catalyst was also reactivated in situ about halfway through the testing, as described in Example 18 below.

DESCRIPTION OF THE PREFERRED EMBODIMENTS

For the purposes of promoting an understanding of the principles of the invention, reference will now be made to various embodiments and specific language will be used to describe the same. It will nevertheless be understood that no limitation of the scope of the invention is thereby intended, such alterations and modifications and such further applications of the principles of the invention as described herein being contemplated as would normally occur to one skilled in the art to which the invention relates.

In accordance with the discussion above, in one embodiment the applicants have discovered a commercially significant process for the preparation of 2,2'-bipyridyls which improves substantially upon those previously known. This preferred process involves reacting a pyridine base at elevated temperature in the presence of a nickel catalyst which comprises a significant amount of elemental nickel bound on a suitable heterogeneous, high-surface area support. This reaction is effectively performed at a temperature of about 200°–240° C. and a pressure sufficient to maintain at least some pyridine base in a liquid state during the reaction. More preferred have been catalysts in which the nonoxidized, elemental nickel present approaches about 100% by weight of the total nickel component, and pressures about equal to or greater than the autogenous pressure of the base at the temperature of the reaction.

Referring now to the catalysts themselves, the support upon which the elemental nickel is dispersed can be one of many suitable heterogeneous supports known in the art which are capable of withstanding these reaction conditions. For example, common supports such as silica, alumina, kieselguhr, and blends of silica and alumina are suitable for the applicants' processes as described herein. Methods for forming the catalysts can include one of several known techniques such as impregnation, precipitation and co-precipitation of a nickel salt on or with the selected support material. Other characteristics such as the size and shape of the support are influenced by many factors including the amount of catalyst surface area desired, the ease and method of handling proposed, desired flow characteristics, and the like. To date, the applicants have effectively used supports shaped as pellets, spheres, extrusions and tablets and having sizes ranging generally from about 1/16-¼ inch in diameter. In any case, the choice of a support, including its size and shape, for use in a particular reaction is both within the skill of those in the art and within the scope of the invention herein.

The applicants have also investigated catalysts having varying degrees of nickel loading on the supports. The catalysts tested thus far in this embodiment have varied from about 30–60% nickel by weight, with the remaining portion being attributable to the support. These catalysts have performed effectively and have been easily prepared by known procedures such as impregnation of the support with a suitable nickel salt such as a nitrate followed by calcination and reduction. See I. Chen and D. Shiue, "Reduction of Nickel-Alumina Catalysts," Ind. Eng. Chem. Res., 27, 429–434 (1988); and I. Chen, S. Lin, and D. Shiue, "Calcination of Nickel/Alumina Catalysts, Ind. Eng. Chem. Res., 2,7 926–929 (1988). Other suitable means, such as by precipitation and co-precipitation, are also known in the art as are many commercially available catalysts from sources such as the Calsicat Division mentioned earlier. From this testing, no minimum threshold or maximum loading of nickel on the support has been shown to exist. It can be said, however, that increased nickel loading has generally produced increased product yields, with the applicants' preferred range of loading thus far being about 50–60% nickel by weight. One exception to this general observation has been where the catalyst is one such as the HTC-400 catalyst discussed in a further preferred embodiment below.

Regarding the state of nickel on the support, the applicants have studied catalysts in which a wide range of the nickel present is in its elemental, activated state. It has generally been found that increasing the elemental nickel content has yielded better results, but without any minimum or threshold level being shown. For that reason, it is considered that any catalyst comprising a significant amount of elemental nickel dispersed or otherwise bound on a suitable, high-surface area support will work in the applicants' process and is within the scope of the invention herein. In this regard, the term "significant" is meant to include an amount of elemental nickel present on the support that is effective in achieving improved rates of 2,2'-bipyridyl production such as those expressed in the specific Examples below. From testing to date, preferred is an elemental nickel content in excess of about 30% by weight of the total nickel component. Particularly with a commercially available catalyst having some initial degree of activation, such as those identified in the paragraph to follow, the applicants have at times increased this activity by an initial pretreatment through heating in a stream of hydrogen or by pretreatment with a sodium borohydride/ammonium hydroxide/methanol solution similar to that described in M. Scaros, H. Dryden, J. Westrich, O. Goodmonson and J. Pilney, "Activation of a Commercially Available Nickel on Alumina Catalyst," *Catalysis of Organic Reactions. Ed. P. Rylander,* 11th Org. Reaction Cat. Soc. (1988). The extent of this pretreatment would then determine the final percentage of elemental nickel present on the catalyst.

In this regard, testing to date has shown one catalyst of choice to be a 56% elemental nickel-on-alumina material marketed by Calsicat under the name Calsicat E-230. Another preferred catalyst from this same source has been Calsicat E-235 which is initially 43% elemental nickel-on-alumina. Still other suitable catalysts for the applicants' process which are marketed commercially for other purposes appear in the Examples below. Sales or advertising literature, where available, is also being provided for each such catalyst and is hereby incorporated herein by reference as to all relevant aspects thereof.

As to conditions for the applicants' process of this embodiment, reactions have been effectively conducted at temperatures of about 200°–240° C. which is above the boiling point of pyridine at atmospheric pressure. More preferred have been temperatures of about 215°–225° C., with most preferred being about 220° C. Except in the applicants' more recent work with HTC-400 catalysts described below, testing has shown that temperatures significantly lower than these result in very low conversions of 2,2'-bipyridyls, while significantly higher temperatures result in rapid catalyst deactivation. To accomplish the preferred reactions, pressures have been maintained in the reaction vessel sufficient to maintain at least some of the pyridine base in a liquid state during the reaction. More preferably, the reactions have been conducted under pressures about at or above the autogenous pressure of the pyridine base at the reaction temperatures used in order to more substantially maintain its liquid state depending on the procedure used.

Referring now to two specific routes to 2,2'-bipyridyl Production which have been favored by the applicants, the first involves a tube reactor through which a stream of pyridine base is pumped preferably in its liquid phase while the second involves a catalytic distillation-type reaction. In the former, 2,2'-bipyridyls have been prepared in effective yields by pumping a liquid stream of pyridine base through a tube reactor which has been packed with an amount of the applicants' supported elemental nickel catalyst as defined above. The tube reactor used thus far has consisted generally of a 4 inch length of ¾ inch diameter stainless steel tubing (0.065 inch wall thickness, 0.62 inch inner diameter, and 19.8 $cm^3$ volume) provided at each end with a Swagelok cap. Once filled, the reactor was immersed in a standard commercially-available hot sand bath, and pyridine base was pumped through the tube at the desired rate using a conventional low-volume, high pressure piston pump. Although many others equally or more suitable exist, applicants to date have used an Eldex A 30 S pump available from Eldex Laboratories, Inc of San Carlos, California. This pump was connected to the reactor via standard ⅛ inch stainless steel tubing. A back-pressure regulator was used to control the pressure of the pyridine within the reactor. The reaction mixture exited the reactor through standard ⅛ inch stainless steel tubing, passed through an air-cooled product condenser and was collected in Whitey stainless steel sample cylinders. Temperatures and pressures have been maintained in the tube reactor consistent with those indicated above. Effective flow rates were varied from about 40–500 g pyridine base/hr with the above reactor, which equates to a space/time velocity from about 2–100 g pyridine base/ml catalyst/hr. These rates in turn gave conversions to 2,2'-bipyridyl product ranging from about 4–1% by weight, respectively, using the preferred Calsicat E-230 catalyst. This inverse relationship of flow rate to product yield is understandable as decreasing the contact time of base with catalyst in the reaction zone would be expected to produce a lower net yield. Nevertheless, this high volume/low net approach may be advantageous in many situations when comparing effective product yields over a certain quantity of catalyst and time period. This relationship may be expressed as grams of 2,2'-bipyridyl produced per gram of nickel catalyst per hour of reaction. A shorthand version of this measurement used in the Examples below is expressed as "g/g/h".

Other considerations such as increased catalyst life and decreased rates of fouling, ease of recycling, equipment capabilities and the like may also lead those skilled in the art to operate under differing flow rates or other conditions in order to maximize the benefits achieved in practicing the applicants' process. Such decisions arc well within the knowledge of such persons, and are within the scope of the invention herein. For example, the unfractionated product outflow has preferably not been recycled back through the reactor because the applicants' work has suggested that this leads to the more rapid inactivation of catalyst. Instead, this reaction mixture has been collected and the 2,2'-bipyridyl removed using conventional distillation techniques before recycling the unreacted base.

In another aspect of the invention, it has been discovered that the pyridine base feed can be spiked with an extremely small amount of a methanolic solution of sodium borohydride and ammonium hydroxide to both activate and extend the useful life of the applicants' catalyst without leading to a significant increase in by-product formation. The preferred spiking or additive solution was prepared by adding 12.6ml of a 29% ammonium hydroxide solution to 40ml of methanol and dissolving 0.6 grams of sodium borohydride in this mixture. Effective results have been observed when the feed stream was spiked with only about 0.1–0.2% by weight of this additive respective runs, as is specifically noted in the Examples below. Optimizing the preparation, amount and use of such an additive solution for a given reaction is within the skill of the art, as is the selection and use of other possible spiking agents. The same are accordingly within the scope of the invention herein.

As already stated, the applicants, second favored route is a catalytic distillation-type procedure. In general, a catalytic distillation involves a process and apparatus wherein both vapor and liquid may be brought in contact with the catalyst held in a column bed with the reaction products being simultaneously separated by fractional distillation from the resulting lower and higher-boiling materials. Further descriptions of such reactions and the equipment employed are ound in U.S. Pat. No. 4,336,407 to Smith and in articles by J. D. Shoemaker et al., "Cumene by Catalytic Distillation," Hydrocarbon Processing (June 1987) and W.P. Stadig, "Catalytic Distillation," Chemical Processing (Feb. 1987), all of which are hereby incorporated herein by reference as to all aspects relevant and material.

To conduct their catalytic distillation-type reactions, the applicants fabricated a conventional pressure still with a column prepared from a 3.5 foot length of stainless steel pipe having a 1.6 inch inside diameter. The column was packed with approximately 1400 grams of catalyst and was set up to operate under increased pressure with a back-pressure regulator used to control the same. The still was also arranged to be operated in batch or continuous modes using common and known techniques. The temperatures and pressures of the reactions were as previously set forth, with the pyridine base preferably just boiling at the conditions selected. For example, for pyridine to boil at a temperature of 220° C., the pressure must be no greater than approximately 133 psig. Under these conditions, a small stream of light ends comprising mostly pyridine with some piperidine and water was taken off the column head at reflux and hydrogen was vented via the back-pressure regulator to maintain the desired pressure. In the batch mode, the distillation still was preferably charged with an amount of pyridine and the reaction allowed to proceed for a set period of time. Thereafter, the product-enriched reaction mixture (containing from about 18–27% by weight 2,2'-bipyridyl) was removed from the bottom of the still and the 2,2'-bipyridyl was recovered using a conventional fractionating column. In the continuous mode, a high reflux ratio was preferably maintained while liquid pyridine was fed into the side of the column into the catalyst bed at about the same rate that the product-enriched reaction mixture was removed from the bottom of the still. Alternatively, a separate fractionating column was established as part of the apparatus to continuously recover the 2,2'-bipyridyl from the product mixture and return the unconverted pyridine base to the reaction zone.

As with the tube reaction, the applicants have discovered that a very small amount of spiking additive can also be used to activate and extend the useful life of their catalyst in this catalytic distillation reaction. To accomplish this, for example, an amount of ammonium hydroxide was combined with the pyridine base fed into the column while hydrogen gas was passed up through the catalyst bed with the refluxing pyridine vapor. Although the amounts used may vary greatly, effective results have been observed with a feed containing only about 0.05% by weight concentrated ammonium hydroxide solution and hydrogen gas bubbled at a rate of only about 6–10 cc/min as measured at the operating pressure of the still. Using this procedure, the applicants have found that catalyst life has more than doubled in many cases before the need for separate reactivation. The applicants have further found that the catalyst, once reactivated as described below, has performed effectively for almost twice as long as the same type of catalyst which was not treated in this manner. These results are more completely discussed in the Examples below.

In yet another aspect of the invention, it has been discovered that the deactivated catalysts can be effectively restored to a large fraction of their former activities by treating them in situ or separately with increased amounts of the same methanolic solution of sodium borohydride and ammonium hydroxide discussed previously in connection with spiking the feed stream to the applicants' tube reactor. More particularly, this reactivation treatment has involved an additive solution prepared by combining the amounts of these ingredients previously described which result in a solution comprising about 1.3% by weight sodium borohydride, about 28.0% by weight ammonium hydroxide and about 70.7% by weight methanol. The restoration treatment using this solution is further discussed in the Examples below.

In addition to the inventive processes described above, the applicants have also discovered additional processes in which certain nickel catalysts can provide successful production of 2,2'-bipyridyls at temperatures as low as about 175° C. In particular, this embodiment relates to a process for preparing 2,2-bipyridyls, which comprises the step of reacting a pyridine base in the presence of a nickel catalyst which includes a significant amount of elemental nickel bound on a suitable support, the nickel having a high specific Ni surface area, the reacting being at a temperature of about 175°–240° C. and at a pressure sufficient to maintain at least some of the base in a liquid state during the reacting. In this regard, the provision of a nickel catalyst having a high specific nickel surface area, i.e. preferably greater than about 100 $m^2$ per gram of nickel, and more preferably a range of 100 to at least about 150 $m^2$/g Ni, provides for effective processes even at the stated lower temperatures. The total nickel content (by weight) of the catalysts of this embodiment can be significantly lower than that of other conventional nickel catalysts such as in the embodiment discussed earlier in this application. For example, this total nickel content can be as low as 10% or below, with at least about 15% being preferred from testing conducted thus far.

In this regard, the preferred catalyst for this embodiment to date has been HTC-400 nickel-on-alumina catalyst which is available from Crosfield Catalysts of Warrington, England. This catalyst contains approximately 15% nickel, and has a very high specific elemental nickel area of about 152 $m^2$/g Ni. In yet other aspects, this HTC-400 catalyst has a pore volume of 0.37 $cm^3$/g, a bulk density of 0.83 g/$cm^2$, a nickel crystallite size of 2.4 nm, a mean pore radius of 71.0 A, a total nickel surface are of 27 $m^2$/g of catalyst, and a degree of reduction from the manufacturer of 85%. Product literature on this HTC-400 catalyst and a family of HTC catalysts is available from Crosfield Catalysts, and such product literature is herewith incorporated by reference in all aspects relevant and material to the invention.

In further aspects of this embodiment, preferred process temperatures are from about 190° to about 210° C. Additionally, it is also preferred that the catalyst used have at least about 85% of the nickel present in its elemental, non-oxidized state. Further preferred aspects and parameters of this embodiment are similar to those of the embodiments discussed above, including two additional specific routes to 2,2'-bipyridyls as discussed above (e.g. tube reactor and catalytic distillation processes) but employing the unique catalysts of this embodiment.

While the invention has been described in detail in the foregoing paragraphs, the same is to be considered as illustrative and not restrictive in character, it being understood that only the preferred embodiments have been described and that all changes and modifications that come within the spirit of the invention are desired to be protected. The following specific Examples are given in further explanation and description of these embodiments, but are also meant to be exemplary and not limiting thereof. For example, while these Examples only disclose the use of pyridine and 2- and 4-methylpyridine as bases for the reactions, it is commonly known and understood by those of ordinary skill in this art that numerous other suitable pyridine bases are available and will work effectively in the reductive coupling reaction of the applicants' process. These additional bases particularly include the lower alkyls and other substituted pyridine derivatives which at least have either their 2- or 6-ring positions available to undergo coupling to thereby produce their corresponding 2,2'-bipyridyls. The term "pyridine base" as used herein is meant to include these many suitable base materials which are accordingly within the intent and scope of the invention herein.

EXAMPLE 1

Tube Reactor Construction

A standard liquid-phase tube reactor for the applicants' process was constructed using a 4-inch length of ⅜-inch stainless steel tubing capped on each end with Swagelok caps. The reactor was immersed in a Techne fluidized sand bath filled with alundum and a Barber-Coleman Limitrol controller was used to regulate the sand bath temperature. The pyridine base was pumped through the reactor tube at the desired flow rate using a 250 ml positive displacement single stroke piston pump, or the Eldex A-30-S previously described. The pyridine base entered the pump through a Teflon tube with a 5 micron stainless steel filter on the end and exited the pump through 1/16-inch stainless steel tubing. This 1/16-inch tubing was connected to separate ⅛-inch stainless steel tubing which led on to the reactor. A back-pressure regulator was used to control the pressure of the feed stream within the reactor which had a capacity of about 19.8 ml and was packed with the desired catalyst material. The product-enriched reaction mixture then exited the reactor through ⅛-inch tubing and was collected in 75 ml capacity Whitey collection cylinders from which fractions could be taken and various components analyzed. The procedures and results obtained using this tube reactor are further discussed in Examples 2 and 3 below.

EXAMPLES 2-15

Investigation of Various Catalysts

The liquid-phase tube reactor of Example 1 was used in several experimental runs to investigate the effectiveness of various supported nickel catalysts in the applicants' preferred process as discussed previously. The reaction conditions and results are set forth in Table I below, with temperature and pressure varying as indicated (it being understood that the autogenous pressure of pyridine at 220° C., for example, is approximately 133 psig). The flow rates of feed through the reactor were maintained at about 80 grams pyridine/hr for purposes of comparison, although other testing had been performed using flow rates varying from about 40 up to about 500 grams pyridine/hr with acceptable 2,2'-bipyridyl yields (see. e.g., Example 20). In addition to the initial activation from the manufacturer of each of the commercial catalysts, which is expressed where available as a percentage by weight of the total nickel component, certain of these catalysts were further reduced to maximize elemental nickel content either by direct activation through extended heating in a stream of hydrogen gas in Examples 4, 5 and 11 or by pretreatment with an excess sodium borohydride/ammonium hydroxide/methanol solution as previously described in Examples 6-9 and 12-15. The approximate elemental nickel content in each of these treated catalysts as tested exceeded 75% and approached 100% by weight of their total nickel component. The 2,2'-bipyridyl yield in each case is expressed as grams of 2,2'-bipyridyl produced per gram of catalyst per hour ("g/g/h"). The pyridine base used as the feed stream in Examples 2-13 was pyridine itself, while the base in Examples 14 and 15 was 2- and 4 methylpyridine, respectively. The corresponding recovered products were 2,2'-bipyridyl in Examples 2 13, was 6,6'-dimethyl-2-2'bipyridyl in Example 14, and was 4,4'-dimethyl-2,2'-bipyridyl in Example 15. In analyzing the results in Table 1, all of the catalysts tested produced acceptable yields of 2,2'-bipyridyl product equal to or surpassing many prior art processes without the numerous problems in handling, scaling up to commercial levels, and the like experienced with the Raney nickel materials. From the results in Table 1, the Calsicat E-230TR catalyst was selected as representative for use in the further investigations reported in the Examples below.

EXAMPLE 16

Catalyst Lifetime Extension in Tube Reactor

Several runs were performed in this Example to test the possible extension of catalyst life and delay of deactivation by use of an additive in the pyridine base feed to the tube reactor of Example 1. In particular, a pyridine feed was spiked with an amount of additive comprising 0.1% by weight of a solution containing 1.3% by weight (0.6 g) sodium borohydride, 28.0% by weight (12.6 ml) concentrated 29% ammonium hydroxide, and 70.7% by weight (40 ml) methanol as described previously in the specification. Calsicat E-230TR was the catalyst used for this study at approximately 40% elemental nickel as provided by the manufacturer, without any further pretreatment or activation. The reaction temperature was maintained at 220° C. and the back-pressure regulator was set at 200 psig. The flow rate observed was about 80 g pyridine/hr. In comparison against an unspiked control, the results confirmed that the inclusion of even this very small amount of additive in the pyridine feed effectively improved catalyst activity and extended its useful life. Without the spiked additive, the g/g/h conversion steadily decreased to about 0.086 after approximately 14 hours of reaction. With only the 0.1% by weight of additive solution, a far more gradual decrease in activity was experienced with a similar g/g/h conversion being maintained in excess of 25 hours of reaction.

In a second set of tests in which the amount of this additive in the pyridine feed was doubled to 0.2% by weight of the above components, respective conversions of 0.126 g/g/h (unspiked) versus 0.147 g/g/h (spiked) were calculated over approximately 8 hours of testing. This confirmed approximately a 16% increase in conversion, and corresponding delay in deactivation, by simply doubling the spiked solution added to the feed stream entering the reactor.

EXAMPLE 17

Catalytic Pressure Still and Use

For use in the Examples to follow, a conventional pressure still with a distillation column was prepared from a 3 ½-foot length of stainless steel pipe having a 1½-inch outside diameter. The still was arranged to operate under increased pressure and a back pressure regulator was used. The still was also arranged using common and known techniques to be operated in a continuous mode if desired. Approximately 1400 g of the Calsicat E-230TR catalyst was divided into four parts, with each part of 350g being first immersed in 700 ml of distilled water with mechanical stirring. A solution of 750 ml methanol containing 235 ml ammonium hydroxide and 11.25 g sodium borohydride was added slowly, and each catalyst part was then stirred for 45 minutes in a pretreatment step to reduce a large percentage certainly in excess of 75% of the total nickel content to its elemental state. Each solution was in turn decanted and the catalyst washed with 4×500 ml portions of distilled water, and the catalyst was stored under distilled water until use.

The column was then packed with the pretreated Calsicat E-230TR catalyst and operated in a continuous mode with liquid pyridine fed into the column near the top of the bed at about the same rate that the product-enriched reaction mixture was removed from the reboiler at the bottom of the still. During this time, the catalyst in the column was maintained at a temperature between about 215°-225° C., and the pressure in the still was maintained at about 135 psig which approximated the autogenous pressure of pyridine at this temperature range. A small stream of light ends comprising mostly pyridine with some piperidine and water was also taken from the column head during reflux, and excess hydrogen was vented off via the back pressure regulator. Midway through this testing, the catalyst was reactivated in situ according to the procedure set forth in Example 19 below. The results obtained from these runs confirmed this to be a highly effective process for producing 2,2'-bipyridyls in which the average conversion was 0.027 g/g/h over an excess of 92 hours of operation. FIG. 1 illustrates these successful results based on data points obtained from actual calculations of average conversions achieved over this extended period.

EXAMPLE 18

Catalyst Lifetime Extension in Distillation Reactor

The still apparatus of Example 17 was used in this experiment with pyridine remaining the base feed, except that this stream was spiked with 0.05% by weight of a concentrated ammonium hydroxide solution. Gaseous hydrogen was also passed up through the catalyst bed at a rate of about 6–10 cc/minute as measured at operating pressure in an effort to improve and extend catalyst activity similar to that achieved in the tube reactor process of Example 16. The results confirmed that this spiking solution in fact increased the rate of formation of 2,2'-bipyridyl while also extending effective catalyst life. In this regard, the average conversion remained at the highly acceptable level of 0.048 g/g/h after in excess of 187 hours of operation. Temperatures and pressures were maintained as in Example 17, and there was similarly one reactivation of the catalyst in situ after about 100 hours of operation. The catalyst had also received a similar pretreatment as in Example 17 to maximize the elemental nickel present on the support at the time the reaction began. The successful results of this testing is shown graphically in FIG. 2 accompanying the specification.

EXAMPLE 19

Independent Reactivation of Catalyst

In this Example, the applicants sought to confirm their discovery for effectively reactivating their catalyst in situ or separately in connection with both the tube reactor and the catalytic distillation still. For the catalyst used in the tube reactions in Examples 2–16 above, in situ reactivation or regeneration was accomplished by pumping a solution containing 1.3% by weight sodium borohydride, 28.0% by weight concentrated ammonium hydroxide and 70.7% by weight methanol at ambient temperature and at pressures of about 75–200 psig through the reactor for about 4–5 hours. Alternatively, the catalyst was removed from the tube reactor and reactivated separately in a batch mode using a solution having the same composition. In the distillation reactors as used in Examples 17–18, reactivation of catalyst was accomplished in situ by pouring a similar solution as described above down through the catalyst bed in the column while a stream of nitrogen gas was bubbled up through the bed to increase agitation. In all cases, this method of reactivation was successfully used in several runs to restore the applicants' catalysts substantially to their initial levels of activity as confirmed by subsequent testing and comparison of relevant conversions achieved.

EXAMPLE 20

Investigation of High Flow Rates in Tube Reactor

In this Example, an amount of Calsicat E-230TR catalyst was initially activated by pretreatment with a solution containing 1.3% by weight sodium borohydride, 28.0% by weight ammonium hydroxide, and 70.7% by weight methanol according to procedures above in order to maximize the elemental nickel content prior to use. This catalyst was then packed in the tube reactor of Example 1 and a pyridine feed containing 0.2% by weight of this same additive solution was begun. The temperature and pressure were maintained at 220° C. and 220 psig, respectively, and the flow rate was increased to 500 g pyridine/hr (e.g., about 100 g pyridine base/ml catalyst/hr in space/time velocity) with the resulting average conversion of 0.223 g/g/h over 31.4 hours of continuous operation. This experiment confirmed that even though high flow rates may result in lower yields in a batch or single pass system, the increased throughput through the reactor and decreased contact time of the 2,2'-bipyridyl product with the catalyst to cause deactivation or fouling may yet be preferred as the overall space time conversion in terms of g/g/h may be increased over time in a given reaction system.

EXAMPLE 21

Catalyst Preparation by Coprecipitation

As one example of an alternate method for preparing catalysts suitable for use in the applicants' inventive process, a nickel-alumina catalyst was prepared at a constant pH using the coprecipitation method described in Kruissink, van Reijen and Ross, J. Chem. Soc. Faraday Trans. I, 77. 649 (1981). A copy of this article accompanies this application and is hereby incorporated herein by reference as to all relevant and material aspects. In particular, using the procedure in this article, nickel and aluminum nitrates were used to prepare a 50% nickel-alumina coprecipitated catalyst which was dried in air and calcined at 400° C. Before use, the catalyst was activated with treatment using a methanol solution of sodium borohydride and ammonium hydroxide as used in earlier Examples. This catalyst was then tested with the liquid-phase tube reactor and according to the procedures described Examples 1 and 2–15 above. Satisfactory yields of 2,2'-bipyridyl from an original pyridine feed were obtained, affording a conversion at or above 0.110 g/g/h over an extended period.

EXAMPLE 22

High Specific Nickel Surface Area Catalysts and Processes

HTC-400 nickel-on-alumina catalyst from Crosfield Catalyst was used for this study. This HTC-400 catalyst is about 15% by weight nickel. The catalyst was initially activated according to the method of Scaros et al., supra, with a methanolic solution of sodium borohydride (0.6 g) and ammonium hydroxide (12.6 ml of a 29% aqueous solution). The catalyst was rinsed with distilled water and packed into the reactor of Example 1. The feed to the reactor was pyridine (80 g/hour), spiked with approximately 0.1% of a solution of similar composition to the methanolic solution used for the initial activation. The reaction temperature was maintained at about 190° C. with the back-pressure regulator set at 220 psig. Under these conditions, conversion of pyridine was 0.1176 g/g/h over 10 hours of operation, and a 0.0784 g/g/h obtains over 32 hours of operation.

Additional experiments were sucessfully carried out under similar conditions, with the temperature of the reactor varying from about 180° to about 220° C. For example, at 200° C., over 32.1/hours of operation (on approximately 6h/day basis) the average conversion (g 2,2 bipyridine/g catalyst/hour) was 0.1130 g/g/h. At 180° C., conversion over a similar time is about 0.05 g/g/h. The significance of these conversions is enhanced because it is calculated on total weight of catalyst packed to the reactor, not on the total weight of Ni present in the catalyst, and further because the HTC-400 catalyst used contains approximately 27% by weight of the amount of nickel contained in the preferred Calsicat E 230 TR catalyst used in other experiments described herein.

What is claimed is:

1. A process for the preparation of 2,2'-bipyridyls, comprising the step of reacting a pyridine base in the presence of a nickel catalyst which comprises a significant amount of elemental nickel bound on a suitable support, said nickel having a high specific nickel surface area, and said reacting being at a temperature of about 175°-240° C. and a pressure sufficient to maintain at least some of the base in a liquid state during said reacting.

2. The process of claim 1 wherein said catalyst is HTC-400.

3. The process of claim 1 wherein the nickel on the support has a specific nickel surface area of at least about 100 $m^2$/g Ni, and wherein said reacting is at a pressure about equal to or greater than the autogenous pressure of the pyridine base at the temperature of said reacting.

4. The process of claim 3 wherein at least about 85% by weight of the nickel present on the support is in its elemental state.

5. The process of claim 4 wherein the catalyst is in the shape of pellets, spheres, extrusions or tablets in a size ranging generally from about 1/16-¼ inch in diameter.

6. The process of claim 1 or 5 wherein said reacting is in a liquid phase tube reactor additionally comprising the steps of charging the tube reactor with an amount of catalyst, bringing the charged reactor to the temperature and pressure of said reacting, and feeding a stream of pyridine base therethrough at a flow rate of about 2-100 grams pyridine base per ml catalyst per hour.

7. The process of claim 6 additionally comprising the steps of isolating and recovering the 2,2'-bipyridyl formed from the product-enriched reaction mixture after said feeding.

8. The process of claim 7 wherein said catalyst is HTC-400 and said reacting and said bringing are at a temperature between about 190-°210° C. and at a pressure of at least about 130 psig.

9. The process of claim 8 additionally comprising the step of treating the catalyst with an activating solution containing a borohydride salt and ammonium hydroxide.

10. The process of claim 9 additionally comprising the step of adding about 0.1-0.2% by weight of said treating solution to the feed stream during said feeding.

11. The process of claim 10 wherein the pyridine base in the feed stream comprises pyridine and the recovered product is 2,2'-bipyridyl.

12. The process of claim 11 wherein said reacting and said bringing are at a temperature of about 190° C. and said feeding comprises pumping the base through the charged and heated tube reactor.

13. The process of claim 1 or 5 wherein said reacting is in a catalytic distillation reactor and additionally comprises the steps of charging a distillation column with an amount of catalyst, bringing the column to the temperature and pressure of said reacting, and introducing a feed of pyridine base.

14. The process of claim 13 wherein fresh pyridine base is supplied to the column for reaction and the 2,2'-bipyridyl formed in the catalyst bed is taken off the bottom of the column in the product-enriched reaction mixture.

15. The process of claim 14 additionally comprising the steps of isolating and recovering the 2,2'-bipyridyl formed from the product-enriched reaction mixture.

16. The process of claim 15 wherein said catalyst is HTC-400 and said reacting and said bringing are at a temperature between about 190°-210° C. and at a pressure sufficient to establish a high reflux ratio in the column.

17. The process of claim 16 additionally comprising the steps of adding at least about 0.05% by weight of ammonium hydroxide to the feed stream and passing hydrogen gas up through the catalyst bed during the reaction.

18. The process of claim 17 additionally comprising the step of treating the catalyst with an activating solution containing a borohydride salt and ammonium hydroxide.

19. The process of claim 18 wherein the pyridine base in the feed comprises pyridine and the recovered product is 2,2'-bipyridyl.

20. The process of claim 19 additionally comprising the steps of isolating and recovering any by-products distilled off the top of the column during the reaction.

21. The process of claim 1 and additionally comprising the step of treating the catalyst with an activating solution containing a borohydride salt and ammonium hydroxide.

22. The process of claim 21 wherein said treating is prior to said reacting.

23. The process of claim 21 wherein said treating is during said reacting.

24. The process of claim 21 wherein said treating is after said reacting.

25. The process of claim 21 wherein the pyridine base in the feed comprises pyridine and the recovered product is 2,2'-bipyridyl.

* * * * *